United States Patent [19]

Inoue et al.

[11] Patent Number: 5,210,033
[45] Date of Patent: May 11, 1993

[54] PROCESS FOR PREPARING AND SELECTING HYPERPRODUCING MICROORGANISM STRAINS USED FOR THE PROCESS FOR PRODUCING STREPTOVARICIN C

[75] Inventors: Kaname Inoue, Kanagawa; Motohide Yamazaki; Kanji Murofushi, both of Niigata, all of Japan; Richard W. Armentrout, La Jolla, Calif.

[73] Assignees: Shin-Etsu Bio, Inc., San Diego, Calif.; Shin-Etsu Chemical Co., Ltd., Tokyo, Japan

[21] Appl. No.: 872,519

[22] Filed: Apr. 23, 1992

Related U.S. Application Data

[62] Division of Ser. No. 776,989, Oct. 16, 1991.

[51] Int. Cl.$^5$ .................... C12N 1/16; C12N 1/36; C12P 17/18; C12P 17/08
[52] U.S. Cl. .................... 435/172.1; 435/119; 435/124; 435/253.5; 435/253.6; 435/244; 435/245; 435/803; 435/886
[58] Field of Search ............ 435/119, 244, 245, 253.5, 435/253.6, 124, 886, 803, 172.1

[56] References Cited

U.S. PATENT DOCUMENTS

| | | | |
|---|---|---|---|
| 5,114,846 | 5/1992 | Inoue et al. | 435/119 |
| 5,126,254 | 6/1992 | Endo et al. | 435/119 |
| 5,137,825 | 8/1992 | Inoue et al. | 435/119 |
| 5,156,961 | 10/1992 | Inoue et al. | 435/124 |

*Primary Examiner*—Herbert J. Lilling
*Attorney, Agent, or Firm*—McAulay Fisher Nissen Goldberg & Kiel

[57] ABSTRACT

Disclosed is a method for selecting a mutant strain belonging to the genus Streptomyces which is a hyperproducer of Streptovaricin C superior to those know heretofore. This is accomplished by first subjecting a natural strain of *Streptomyces spectabilis* to conditions so as to isolate organisms which are streptovaricin resistant. The streptovaricin resistant organisms thus isolated are then subjected to mutagenesis and then cultured. The colonies which are asporogenous are individually cultured in fermentation batches such that the strains take the form of pellets of varying sizes and colors. From the batch having the most heterogeneous mixture of pellets, the smallest pellet or the pellet(s) having the deepest color (usually deep red or crimson) is isolated. We have discovered that the strain of this pellet has a high likelihood of being a hyperproducer of streptovaricin. The strain of this pellet may then be subjected to fermentation conditions to produce streptovaricin. The nutrient broth containing fumaric acid or water-soluble salts thereof, and adsorbent polymer beads and the streptovaricin produced are recovered in the usual manner. In another embodiment, the fermentation may be carried out in a nutrient broth wherein fumaric acid or its water-soluble salts are deliberately excluded to achieve even higher productivity.

6 Claims, No Drawings

PROCESS FOR PREPARING AND SELECTING HYPERPRODUCING MICROORGANISM STRAINS USED FOR THE PROCESS FOR PRODUCING STREPTOVARICIN C

This is a division of application Ser. No. 07/776,989, filed Oct. 16, 1991.

BACKGROUND OF THE INVENTION

This invention relates to a process for the production of Streptovaricin C.

U.S. Pat. No. 3,116,202 describes streptovaricins and their production. As disclosed therein, *Streptomyces spectabilis* (NRRL2494) produces five types of streptovaricins designated as types A, B, C, D, and E. It also describes the use of streptovaricin as an antituberculosis drug. However, this product has not achieved broad use for this purpose.

Example 3 of this patent discloses the accumulation of 21 mg/l of streptovaricin in the broth assuming that the crude product was 100% pure. However, the disclosure gives no indication of the amount or ratio of Streptovaricin C in the crude mixture.

More recent attempts have been made to obtain novel antibiotics by chemically modifying Streptovaricin C in order to provide anti-virus and anti-cancer agents (See K. Onodera et al., *The Journal of Antibiotics*. February 1986, pp.147–154). (See K. Onodera et al., *The Journal of Antibiotics*, May 1989, pp. 779–787.)

These derivatives use only Streptovaricin C and thus require a method for selectively preparing Streptovaricin C. In the May 1989 K. Onodera et al article, the yield of Streptovaricin C, the most abundant component of the streptovaricin complex provided by the Upjohn Co. and used by the authors, was about 20%. (See pages 151-152).

In K. Rinehart et al., *Biochemistry*, Vol. 13, No. 5, 1974, pp. 861–867, the content of Streptovaricin C within the mixture of streptovaricins obtained from the provider (Upjohn 11560-3), was about 10 to 20%. This suggests that the Streptovaricin C content in the broth of Example 3 of U.S. Pat. No. 3,116,202 was about 2–4 mg/l. These amounts and concentrations are not sufficient for further development of Streptovaricin C derivatives.

A more efficient method for separating Streptovaricin C from a culture broth of a streptovaricin producing strain which produces a mixture of types A, B, C, D, and E, is disclosed in Japanese applications No. 14285/1990 and 14286/1990. (See also H. Wang, Annals New *Academy of Sciences*, 431, 1983, pp.313–321.) In these methods, a publicly available streptovaricin-producing strain (ATCC 27465) is cultured in the presence of a non-ionic adsorbent and with the optional addition of fumaric acid or one of its water-soluble salts. Using these methods, it was possible to increase the amount of Streptovaricin C separated from the culture broth. Even so, higher productivity of streptovaricin is needed for proper development and commercial production of this compound.

U.S. patent application Ser. Nos. 07/601,875 and 07/601,877, filed on Oct. 23, 1990, respectively, the contents of each of which are incorporated herein by reference, disclose methods for increasing the efficiency of producing and separating Streptovaricin C from a culture broth. This is achieved by carrying out the fermentation in the presence of a nonionic adsorbent, e.g., in the form of beads, and effecting separation of the beads from the fermentation broth by adjusting the specific gravity of the fermentation broth.

U.S. patent application Ser. No. 07/601,876, filed Oct. 23, 1990, the contents of which are incorporated herein by reference, discloses a method for selectively producing Streptovaricin C from a culture broth resulting in isolation of Streptovaricin C and a method for selecting a natural mutant strain belonging to the genus Streptomyces which is a hyper-producer of Streptovaricin C. The hyperproducing strain obtained by this method produced streptovaricin in an amount of about 600 to 700 mg/liter. This strain has been deposited at the Fermentation Institute in Japan under Deposit No. FERM BP-3460. The Streptovaricin C hyperproducing strains are selected from *Streptomyces spectabilis* by culturing *Streptomyces spectabilis*, and separating those colonies which are non-spore forming (asporogenous). The selected colonies are then separately cultured and tested for streptovaricin productivity. The colony or colonies having the highest desirable streptovaricin productivity is then fermented in a nutrient broth containing a compound selected from the group consisting of fumaric acid and water-soluble salts thereof, and adsorbent polymer beads and the streptovaricin produced are recovered in the usual manner.

SUMMARY OF THE INVENTION

We have discovered a method for selectively producing Streptovaricin C from a culture broth in yields higher than heretofore achievable. More particularly, we have discovered a method for selecting a mutant strain belonging to the genus Streptomyces which is a hyper-producer of Streptovaricin C superior to those know heretofore.

In accordance with the invention, we have found that Streptovaricin C hyperproducing strains can be easily and quickly selected from *Streptomyces spectabilis* by first subjecting a natural strain of *Streptomyces spectabilis* to conditions so as to isolate organisms which are streptovaricin resistant. The streptovaricin resistant organisms are then subjected to mutagenesis, preferably ultraviolet mutagenesis. However, other types of mutagenesis treatments may be used. e.g., chemical mutagenesis. The thus treated organisms are cultured and the colonies which are non-spore forming (asporogenous) are individually cultured in fermentation batches such that the strains take the form of pellets of varying sizes and colors. From the batch having the most heterogeneous mixture of pellets from the standpoint of size and/or color, the smallest pellet or the pellet(s) having the deepest color (usually deep red or crimson) is isolated. We have discovered that the strain of this pellet has a high likelihood of being a hyperproducer of streptovaricin.

The strain of this pellet may then be subjected to fermentation conditions to produce streptovaricin. This is preferably carried out in a nutrient broth containing a compound selected from the group consisting of fumaric acid and water-soluble salts thereof, and adsorbent polymer beads and the streptovaricin produced are recovered in the usual manner.

In another embodiment, we have discovered that by fermenting the colony or colonies having the highest desirable streptovaricin productivity in a nutrient broth wherein fumaric acid or its water-soluble salts are deliberately excluded from the broth, even higher productivity of streptovaricin can be obtained.

DETAILED DESCRIPTION OF THE INVENTION

*Streptomyces spectabilis* is first subjected to treatment to isolate those organisms which are streptovaricin resistant. This is usually achieved by mixing a given strain of *Streptomyces spectabilis* in a sterile physiological saline containing Streptovaricin C. The Streptovaricin C concentration may be in the range from about 0.1 to 5.0 mg/10 ml of saline. The original strain is normally diluted with sterilized physiological saline prior to introduction into the Streptovaricin C containing saline. The concentration of the streptovaricin is not critical. However, it should be sufficient so as to effect a substantial reduction in the total organisms, but leave surviving organisms for further treatment.

The solution is then incubated for a given time period to produce a culture which can be further treated in accordance with the invention. Alternatively, the microbes can be separated from the culture and frozen to produce a freeze-stock for subsequent use.

Thereafter, the culture thus produced or the freeze-stock therefrom, upon dilution with an appropriate physiological saline or equivalent, is inoculated onto agar or other conventional nutrient plates and the plated material is subjected to mutagenesis. This can be accomplished using the conventional mutagenizing methods, e.g., irradiation, treatment with chemical mutation agents, and the like. Typical mutagenesis agents include N-methyl-N'-nitro-N-nitrosoguanidine, methyl- and ethylmethanesulfonic acid, sodium nitrite, sodium bisulfite, hydroxylamine, nucleic acid base analogs, such as, 2-aminopurine and 5-bromouracil, and acridine dyes, such as, proflavine. (See Methods for mutagenesis are disclosed in Manual of Industrial Microbiology and Biotechnology, Arnold L. Demain and Nadine A. Solomon (Ed.), Mutagenesis in Streptomyces spp., Richard H. Baltz.)

The thus treated organisms are incubated and grown for a period of four days at an appropriate temperature, e.g., 27° C. or other temperature satisfactory for growth of the colonies.

The colonies have a distinct appearance, being either pale yellow or white and covered with spores. However, a relatively small number of non-symmetrical, asporogenous colonies are observed. Asporogenous colonies are easily identified on the plate by visual inspection because the asporogenous colonies have a distinctive smooth surface. The normally produced reddish pigment is not obscured by spores. The non-symmetrical colony types include both spore forming and asporogenous colony types. However, the asporogenous colony types have a non-symmetrical colony form on the plates.

The asporogenous colonies were selected and cultured in separate fermentation batches whereby the organisms formed pellet-like beads in the liquid mixture. The homogeneity of the mixtures varied from batch to batch. Those batches wherein the pellets were all of similar size are classed as homogeneous. Those batches wherein the pellets were of varying sizes and/or colors usually ranging from whitish to deep red were classified as non-homogeneous, A non-homogeneous batch was selected, and from this batch, the smallest and/or most deeply colored pellet(s) is selected. This can be carried out by simple pipetting techniques. It is desirable to clean the strain to purify it prior to using the strain for production of streptovaricin. This can be accomplished by rinsing and/or replating the pelletized strain. When the strain is replated, the colony which is most uniform, i.e., in color, symmetry, and the like, is selected as representing the purest culture. The thus purified strain may then be subjected to fermentation conditions as described hereinbelow.

As used herein, a hyperproducing strain is one which produces Streptovaricin C in an amount of at least about 1000 mg/l.

The variant thus selected may be cultured in a conventional manner using a nutrient broth. Such nutrients may contain an assimilable carbon source, such as, starch, dextrin, glucose, sucrose, lactose, and the like; an organic nitrogen source, such as, corn steep liquor, peptone, meat extract, yeast extract, vegetable protein, casein, malt extract, dry yeast, soybean meal, and the like, and/or an inorganic nitrogen source, such as, ammonium sulfate, ammonium nitrate, potassium nitrate, and the like. Minerals may also be present, such as, calcium carbonate, potassium phosphate, magnesium sulfate, potassium chloride, sodium chloride, zinc sulfate, ferrous sulfate, manganese sulfate, cobalt chloride, ammonium molybdenate, and the like, as well as mixtures of these minerals.

The culture broth further contains adsorbent polymer beads which are porous and have a relatively large specific surface area. Such polymer beads are well known in the art and described in U.S. patent application Ser. No. 07/601,875, filed Oct. 23, 1990, referred to hereinabove. Such polymer beads can be made by polymerizing various types of monomers, e.g., styrene, bivinyl benzene, acrylic acid ester, methacrylic acid ester, as well as copolymers thereof.

Commercially available examples of such beads are HP-10, HP-20, HP-30, HP-40, HP-50 (Mitsubishi Chemical Co.); and XAD-2, XAD-4 (Rohm & Haas Co.). These beads are all co-polymers of styrene and divinyl benzene. XAD-7 (Rohm & Haas Co.), which is an acrylic co-polymer, may also be used.

Typically, these beads have a diameter of from 50 to 1,000 micrometers, a specific surface area in the range of from 50 to 1,000 $m^2/g$ and a specific pore volume in the range from about 0.2 to 1.5 ml/g. The most preferable of the above-noted commercial products are HP-20, and XAD-4.

In one embodiment of the invention, the culture broth may contain fumaric acid and/or a water-soluble salt thereof. Typical salts includes sodium fumarate, potassium fumarate, potassium sodium fumarate, monosodium fumarate, monopotassium fumarate, and the like, as well as mixtures thereof.

However, we have further discovered, when the selection process is carried out as disclosed herein, with the exception that fumaric acid or its water-soluble salt is excluded from the nutrient broth, yields of Streptovaricin C in excess of 2000 mg/liter can be achieved.

The fermentation itself may be carried out using conventional procedures, including temperatures, pH values for the broth, and the like. The amount of nutrients used as outlined above may be varied as necessary. The amount of fumaric acid or its salt, when it is used, is preferably in the amount from about 0.1 to 10 percent and, most preferably, from about 0.5 to 5 per cent by weight. While the broth components are normally added at the beginning of the fermentation, they can be added repeatedly as needed during the progress of the fermentation.

Suitable pH conditions for the fermentation range from about 4.0 to 9.0 and the temperature is from about 20° to 37° C., preferably, from about 20° to 30° C. The fermentation can be continued for approximately 4 to 20 days to accumulate the desired amount of Streptovaricin C. During the process, the broth is sampled periodically to determine the product concentration. Usually, this is done by taking a sample of the broth, separating the broth from the beads by filtration or other means, e.g., adjusting the specific gravity of the sample, and extracting the product from the beads with an organic solvent. The amount of Streptovaricin C in the sample is determined by high performance liquid chromatography (HPLC). Normally, the fermentation is stopped when the maximum amount of product is obtained.

Organic solvents which can be used for the extraction include methanol, ethanol, acetone acetonitrile, ethyl acetate, methylene chloride, chloroform, and the like, as well as mixtures thereof. The streptovaricins in the product can be roughly separated so as to concentrate the Streptovaricin C using gradient mixtures of solvent and water. The solvent is extracted and the residue is suspended in a small amount of solvent, and filtered, if necessary. A solvent, e.g., n-hexane can be added to precipitate crude streptovaricins. Standard chromatography and recrystallization, or large scale HPLC can be use to separate and purify the streptovaricins.

The following examples illustrate the invention:

EXAMPLE 1

A. Production of a Streptovaricin C Resistant Strain

A stock dispersion solution of *Streptomyces spectabilis* ATCC27465 which contained about $6 \times 10^6$ microbes/ml was diluted at a ratio of 1:1000 using sterilized physiological saline. 1 ml of this diluted solution was mixed with 9 ml of sterilized physiological saline containing 2.0 mg of Streptovaricin C. The solution was maintained at 27° C. for one day. (Several concentrations of Streptovaricin C were tried and the 2 mg concentration was selected as being the highest concentration at which growth could be sustained.)

This treated solution was then inoculated into 100 ml of sterile Seed Medium having the following composition:

| | |
|---|---|
| Hydrolyzed casein (N-Z Amin A) | 12.5 g/l |
| Glucose | 6.25 |
| Enzyme-decomposed extract of soybean (Soytone) | 6.25 |
| K₂HPO₄ | 1.56 |
| KH₂PO₄ | 1.56 |

The thus inoculated medium was incubated for four days at 27° C. on a rotary shaker at a speed of 175 rpm. Thereafter, the microbe in the thus cultured medium was centrifuged, diluted to 20 ml with 20% glycerol, and frozen to make Freeze-Stock No. 1.

B. Subjecting Strain to Mutagenesis

Freeze-stock No. 1 was diluted 1:1000 and 0.2 ml of this diluted solution was added to each of twenty five agar plates containing 15 ml of the following Inoculum Medium:

| | |
|---|---|
| Normal bouillon | 18.0 g/l |
| Glucose | 6.25 |
| Yeast extract | 2.0 |
| Agar | 15.0 |

Groups of five plates each were exposed to ultraviolet irradiation for 0, 2, 3, 4, and 5 minutes using a 15 watt germicidal lamp (Hitachi GL 15) at a distance of 80 cm above the plates.

The plates were then incubated for at 27° C. After two days, the groups of plates were examined and the total number of colonies in each group at each exposure condition was as follows:

| | |
|---|---|
| 0 minutes exposure | 1154 |
| 2 minutes exposure | 1111 |
| 3 minutes exposure | 24 |
| 4 minutes exposure | 35 |
| 5 minutes exposure | 22 |

The plates were further incubated for 7 days. From the plates having been exposed for four minutes to ultraviolet lights, an asporogenous colony was selected and inoculated into 100 ml of sterile Seed Medium having the composition described hereinabove.

This culture was further incubated for three days at 27° C. on a rotary shaker at 175 rpm. The microbes were centrifuged, diluted with 25 ml of 20% glycerol and frozen to prepare Freeze-Stock No. 2.

C. Preparation of Preproduction Culture 0.5 ml of freeze-stock No. 2 were inoculated into 100 ml of sterile Preproduction Medium having the following composition:

| | |
|---|---|
| Corn dextrin | 10.0 g/l |
| Defatted soybean meal | 10.0 |
| Corn steep liquor | 10.0 |
| Beer yeast | 2.5 |
| KCL | 3.0 |
| CaCO₃ | 4.0 |

The thus inoculated Preproduction Medium was incubated for three days at 27° C. on a rotary shaker at 175 rpm to produce a Preproduction Culture.

5 ml of the thus obtained Preproduction Culture were inoculated into 100 ml of a sterile production medium No. 1 having the following composition:

| | |
|---|---|
| Glucose | 60.0 g/l |
| Soybean meal | 20.0 |
| Beer yeast | 10.0 |
| NaCl | 0.5 |
| K₂HPO₄ | 2.5 |
| Monosodium fumarate | 24.0 |
| Silicone defoamer (KM75) | 2.0 |
| Polystyrene-type adsorbent beads (HP-20; 50% solid) | 100.0 |

This culture was incubated for 11 days at 27° C. on a rotary shaker at 175 rpm. For comparison purposes ATCC strain 27465 and FERM BP-3460 were incubated utilizing same Production Medium No. 1 and under the same conditions.

After 11 days of fermentation, the Streptovaricin C accumulation in each of the three cultures was determined by HPLC. The results are as follows:

| | |
|---|---|
| Freeze-Stock No. 2 | 442 mg/l |
| ATCC 27465 | 98 |
| FERM BP-3460 | 606 |

D. Purification of Selected Colonies:

Freeze Stock No. 2 was further purified as follows: 100 ml of the sterile Preproduction Medium were inoculated with 0.5 ml of Freeze-Stock No. 2 and incubated for three days at 27° C. on a rotary shaker at 175 rpm. Visual observation of the cultures showed the formation of the microbes into small pellets having various colors ranging from crimson to pale brown. An approximately 5 ml sample of the broth was analyzed as to the size, color, and size of the pellets. The classification was as follows:

| | |
|---|---|
| Small crimson pellet | 3 |
| Large red pellet | 9 |
| Large reddish brown pellet | 70 |
| Large pale brown pellet | 1500 |

(Small pellets had diameters of about 0.1 to 0.3 mm, and large pellets are those having diameters larger than about 0.3 mm.; the color of the pellets ranged from deep red, i.e., crimson, to red to reddish brown to pale brown). As will be seen herein, the hyperproducing stain is the organism formed into the smallest and most deeply colored, i.e. crimson, pellet.

Pellets typifying the spectrum of colors were selected from the preproduction culture, washed twice with 10 ml of sterile physiological saline. Each thus selected and washed pellet was inoculated onto an agar plate containing 8 ml of Inoculum Medium described hereinabove by streaking the pellet onto the medium. The thus prepared plates were incubated for four days at 27° C.

A geometrically symmetrical colony was picked from each plate and inoculated into 100 ml of sterile Seed Medium as described hereinabove. The inoculated Seed Medium was incubated for three days at 27° C. on a rotary shaker at 175 rpm to produce a series of seed cultures. The microbes in each culture were centrifuged to separate them and identified as Freeze-Stocks A B, C, D, E, F, G and H.

0.5 ml of each of Freeze-Stocks A through H was inoculated into 100 ml of sterile Preproduction Medium as described above and incubated for 3 days at 27° C. on a rotary shaker at 175 rpm to produce a Preproduction Culture. 5 ml of each of the Preproduction Cultures of freeze-stocks A through H were inoculated into 100 ml of Production Medium No. 2 having the following composition:

| | |
|---|---|
| Glucose | 90.0 g/l |
| Soybean meal | 20.0 |
| Beer yeast | 10.0 |
| NaCl | 0.5 |
| K$_2$HPO$_4$ | 2.5 |
| Monosodium fumarate | 24.0 |
| Silicone defoamer (KM75) | 2.0 |
| Polystyrene-type adsorbent beads (HP-20; 50% solid) | 100.0 |

Each of these cultures was incubated for 18 days at 27° C. on a rotary shaker at 175 rpm. In addition ATCC 27465 and FERM BP-3460, were incubated under the same conditions and for the same timer period for purposes of comparison.

The accumulated Streptovaricin C in each of the 10 cultures as determined by HPLC are shown in Table 1.

TABLE 1

| | |
|---|---|
| Freeze-stock A (small crimson pellet) | 1084 mg/l |
| Freeze-stock B (small crimson pellet) | 1163 |
| Freeze-stock C (small crimson pellet) | 1127 |
| Freeze-stock D (large red pellet) | 587 |
| Freeze-stock E (large red pellet) | 702 |
| Freeze-stock F (large reddish brown pellet) | 439 |
| Freeze-stock G (large reddish brown pellet) | 459 |
| Freeze-stock H (large, pale brown pellet) | 341 |
| ATCC 27465 | 106 |
| FERM BP-3460 | 650 |

As can be seen, the strains of Freeze-Stocks A, B, and C, produced significantly increased concentrations of Streptovaricin C, indeed, in excess of 1000 mg/l as compared to the other Freeze-Stocks and comparison strains.

The *Streptomyces spectabilis* strains of Freeze-Stocks A, B, and C have been deposited subject to and under the provisions of the Budapest Treaty on the International Recognition of the Deposit of Microorganisms for the Purpose of Patent Procedure at the Fermentation Research Institute at 103, Higashi 1-Chome, Tsukuba-shi, Ibaraki-ken, 305, Japan, on Oct. 9, 1991 as follows:

| | Accession No. | Depositor Identification No. |
|---|---|---|
| Freeze-Stock A | FERM BP-3598 | 910928-61-1 |
| Freeze-Stock B | FERM BP-3599 | 910928-63-2 |
| Freeze-Stock C | FERM BP-3597 | 910928-35-2 |

EXAMPLE 2

10 separate flasks, each containing 100 ml of the sterile Preproduction Medium as described above were each separately inoculated with 0.5 ml of Freeze-Stock A and incubated for three days at 27° C. on a rotary shaker at 175 rpm to produce 1000 ml of Preproduction Culture.

This total Preproduction Culture was inoculated into 18 l of sterile Production Medium No. 2 in a 30 l jar fermenter. The culture was fermented for 20 days at 27° C. under stirring at 250 rpm and with 1 volume/volume/minute aeration.

At the end of the 20th day, the Streptovaricin C concentration was measured to be 1061 mg/l.

The streptovaricins which accumulated on the HP-20 beads were extracted with $CH_2Cl_2$, which was then removed by evacuation and n-hexane was then added to precipitate the streptovaricins. The Streptovaricin C content of the precipitate obtained was 52.6 per cent by weight as determined by HPLC.

EXAMPLE 3

10 ml of freeze-stock A was inoculated into 3 l of sterile Preproduction Medium in a 5 l jar fermenter. The culture was incubated for three days at 27° C., under stirring at 300 rpm and 1.75 v/v/m aeration. 1000 ml of Preproduction Culture was thus obtained and further inoculated into 18 l of sterile Production Medium No. 2 in a 30 liter jar fermenter. The culture was fermented for 14 days at 27° C. under stirring at 150 rpm and 1 v/v/m aeration. At the 14th day, the Streptovaricin C concentration was 1141 mg/l.

The streptovaricins accumulated on the HP-20 resin were extract with $CH_2Cl_2$ and precipitated by the addition of n-hexane after the evacuation of the $CH_2Cl_2$. The Streptovaricin C content of the total streptovaricins recovered was 55.8% as determined by HPLC.

EXAMPLE 4

0.5 ml of freeze-stock A and Freeze-Stocks from ATCC 27465 as well as FERM BP-3460 were separately inoculated into 100 ml of a sterile Preproduction Medium having the following composition:

| Corn dextrin | 20.0 g/l |
|---|---|
| Defatted soybean meal | 10.0 |
| Corn steep liquor | 10.0 |
| Beer yeast | 2.5 |
| KCl | 3.0 |
| $CaCO_3$ | 4.0 |

This was incubated for 3 days at 27° C. on a rotary shaker at 175 rpm to produce a Preproduction Culture. Thereafter, 5 ml of each of the 3 Preproduction Cultures were inoculated into 100 ml of a sterile Production Medium No. 3 having the following composition:

| Glucose | 120.0 g/l |
|---|---|
| Soybean meal | 20.0 |
| Beer yeast | 10.0 |
| Na Cl | 0.5 |
| $K_2HPO_4$ | 2.5 |
| Silicone defoamer (KM75) | 2.0 |
| Polystyrene-type adsorbent beads (HP-20; 50% solid) | 100.0 |

No fumarate or its salt was used in the Production Medium. This culture was fermented for 17 days at 27° C. on a rotary shaker at 175 rpm. The concentration of Streptovaricin C which accumulated on the adsorbent beads of each of the three cultures was determined at the 7th and 17th day by HPLC. The results are as follows:

|  | 7th Day | 17th Day |
|---|---|---|
| Freeze-stock A | 903 mg/l | 2,257 mg/l |
| ATCC 27465 | 8 | 9 |
| Natural mutant of application FERM BP-3460 | 65 | 80 |

As shown, with this strain, Streptovaricin C yields in excess of 2,000 mg/l can be obtained.

EXAMPLE 5

10 ml of freeze-stock A were inoculated into 2 l of sterile Preproduction Medium as described above prepared in a 5 l jar fermenter. The culture was incubated for 3 days at 27° C. under stirring of 300 rpm and 1.7 v/v/m aeration.

1000 ml of the thus obtained Preproduction Culture were inoculated into 18 l of sterile Production Medium No. 3 in a 30 l jar fermenter. The culture was fermented for 20 days at 27° C. at stirring at 150 rpm and aeration of 1 liter of air per 1 liter of culture per minute. At the 8th day, the Streptovaricin C concentration was measured to be 1,021 mg/l and at the 20th day, the Streptovaricin C concentration was measured to be 2,310 mg/l.

The streptovaricins accumulated onto the HP-20 beads were extracted with $CH_2Cl_2$ and precipitated by adding n-hexane after evacuation of $CH_2Cl_2$. The Streptovaricin C as determined by HPLC was 58.8%.

What is claimed is:

1. A method for the selection of a hyperproducing strain of *Streptomyces spectabilis* comprising:
    a) subjecting a wild-type strain of *Streptomyces spectabilis* to conditions to eliminate non-streptovaricin resistant organisms and to induced mutagenesis;
    b) culturing the streptovaricin resistant strain obtained from step a);
    c) growing a multiplicity of colonies from the culture of step b), and selecting those colonies which are asporogenous;
    d) culturing each asporogenous colony in a separate liquid fermentation mixture so as to form pellets of the strains from each colony; and
    e) selecting from the fermentation mixture containing non-homogeneous pellets, the smallest pellet visible to the naked eye.

2. A method for the selection of a hyperproducing strain of *Streptomyces spectabilis* comprising:
    a) subjecting a wild-type strain of *Streptomyces spectabilis* to conditions to eliminate non-streptovaricin resistant organisms and to induced mutagenesis;
    b) culturing the streptovaricin resistant strain obtained from step a);
    c) growing a multiplicity of colonies from the culture of step b), and selecting those colonies which are asporogenous;
    d) culturing each asporogenous colony in a separate liquid fermentation mixture so as to form pellets of the strains within each colony; and
    e) selecting from the fermentation mixture containing non-homogeneous pellets, the pellet having the deepest crimson color visible to the naked eye.

3. The method of claim 1 wherein the wild-type strain is *Streptomyces spectabilis* ATCC27465.

4. The method of claim 1 wherein mutagenesis is effected by UV irradiation.

5. The method of claim 2 wherein the wild-type strain is *Streptomyces spectabilis* ATCC27465.

6. The method of claim 2 wherein mutagenesis is effected by UV irradiation.

* * * * *